(12) United States Patent
Ceder et al.

(10) Patent No.: US 12,337,188 B2
(45) Date of Patent: Jun. 24, 2025

(54) METHOD AND APPARATUS FOR IMPROVING EYE HEALTH WITH NEAR INFRARED AND VISIBLE LIGHT

(71) Applicants: Kenneth Ceder, Peoria, CA (US); Leonard Ceder, Peoria, AZ (US)

(72) Inventors: Kenneth Ceder, Peoria, CA (US); Leonard Ceder, Peoria, AZ (US)

(*) Notice: Subject to any disclaimer, the term of this patent is extended or adjusted under 35 U.S.C. 154(b) by 0 days.

(21) Appl. No.: 15/942,284

(22) Filed: Mar. 30, 2018

(65) Prior Publication Data

US 2018/0280717 A1     Oct. 4, 2018

Related U.S. Application Data

(60) Provisional application No. 62/479,112, filed on Mar. 30, 2017.

(51) Int. Cl.
| | |
|---|---|
| *H02J 9/02* | (2006.01) |
| *A61F 9/007* | (2006.01) |
| *A61N 5/06* | (2006.01) |
| *F21K 9/232* | (2016.01) |
| *F21W 131/20* | (2006.01) |
| *F21Y 113/00* | (2016.01) |
| *F21Y 113/13* | (2016.01) |
| *F21Y 115/10* | (2016.01) |

(52) U.S. Cl.
CPC ............ *A61N 5/0613* (2013.01); *F21K 9/232* (2016.08); *A61N 2005/0652* (2013.01); *A61N 2005/0654* (2013.01); *A61N 2005/0659* (2013.01); *A61N 2005/0662* (2013.01); *F21W 2131/20* (2013.01); *F21Y 2113/13* (2016.08); *F21Y 2113/30* (2023.05); *F21Y 2115/10* (2016.08)

(58) Field of Classification Search
CPC .......... A61N 5/0613; A61N 2005/0652; A61N 2005/0654; A61N 2005/0659; A61N 2005/0662; F21K 9/232; F21Y 2113/13; F21Y 2115/10
See application file for complete search history.

(56) References Cited

U.S. PATENT DOCUMENTS

| | | | | |
|---|---|---|---|---|
| 7,960,872 | B1* | 6/2011 | Zhai | F21V 7/30 307/157 |
| 2014/0288351 | A1* | 9/2014 | Jones | A61N 5/0624 600/9 |
| 2015/0057701 | A1* | 2/2015 | Kelleher | A61H 23/0245 606/204.15 |
| 2016/0169474 | A1* | 6/2016 | Cai | F21K 9/232 362/311.02 |
| 2017/0231058 | A1 | 8/2017 | Sadwick | |

FOREIGN PATENT DOCUMENTS

| | | |
|---|---|---|
| CN | 1570465 A | 1/2005 |
| CN | 204806002 U | 11/2015 |
| CN | 107654901 A | 2/2018 |
| RU | 157667 U1 | 12/2015 |

\* cited by examiner

*Primary Examiner* — Jon Eric C Morales
(74) *Attorney, Agent, or Firm* — Russ Weinzimmer & Associates, PC; Russ Weinzimmer

(57) ABSTRACT

This invention relates to a method and apparatus that uses light-emitting diodes to provide near-infrared light to improve eye health while simultaneously providing visible spectrum light for illumination.

6 Claims, 3 Drawing Sheets

METHOD AND APPARATUS FOR IMPROVING EYE HEALTH WITH NEAR INFRARED AND VISIBLE LIGHT

BACKGROUND

Infrared light is light that lies between the visible and microwave portions of the electromagnetic spectrum. Infrared light can be divided into "near-infrared" and "far-infrared" regions. "Near-infrared" light is infrared light that is closest in spectrum to visible light, while "far-infrared" light is infrared light that is closest in spectrum to microwaves. Near-infrared light consists of light that is just beyond the visible spectrum. Although definitions can vary, here near-infrared (NIR) light is defined as light falling between approximately 700-1,400 nm in wavelength.

NIR light is emitted and absorbed by many everyday objects. A good portion of the warming effects of the sun on the earth's surface (and people and objects on the surface) is believed to be due to infrared radiation. Since modern humans spend a greater proportion of time indoors, exposure to infrared radiation from the sun and objects that absorb infrared radiation from the sun is lower than for previous generations. Because NIR light is outside the visible spectrum, it does not significantly contribute to the brightness of manufactured light bulbs and other lighting solutions. Consequently, lighting manufacturers focus on the output of light in the visible spectrum, and do not provide significant NIR output in commercial lighting products for homes or offices.

Recent research suggests that long exposure to blue light without significant NIR light can cause damage to the eyes by affecting the Mitochondrian DNA of the retinas. A loss of photoreceptors and the induction of necrosis has been observed after long exposure to blue light from LED's, which is one of the primary means of producing "white light" in many commercial LED products.

Recent research also suggests that light in the near-infrared spectrum can reverse and reduce vision loss due to macular degeneration, and prime retinal cells for repair. One of the mechanisms of NIR action involves the cell's respiration system located in the mitochondria.

Light-emitting diode (LED) bulbs are becoming the standard for many home and office uses. LED bulbs typically offer increased energy efficiency and longer lifespan than traditional incandescent or compact fluorescent (CFL) bulbs. LED bulbs for home or office use typically emit light in the range of 400-750 nanometer (nm) wavelengths, with a majority of the light near 450 nm (blue light) and 550 nm (green light).

It would be useful to have LED bulbs, light therapy devices, and other lighting solutions that provide NIR light to improve eye health in addition to visible spectrum light for illumination.

SUMMARY

Generally, this invention solves the problems described above and others not explicitly stated by using the method and device disclosed herein.

Accordingly, it is an object of this invention to provide a method and device that improves eye health by using light-emitting diodes to provide NIR light, while also providing visible spectrum light for illumination.

These as well as other aspects, advantages, and alternatives, will become apparent to those of ordinary skill in the art by reading the following detailed description, with reference where appropriate to the accompanying drawings.

DETAILED DESCRIPTION

The standard or medium-sized light bulb socket in the United States utilizes an E26 base. The "E" refers to use of the Edison screw fitting system, while the number (in this case 26) refers to the diameter of the base in millimeters. E26 is the standard for nearly all homes in the United States. Most light bulbs constructed with an E26 base are compatible with the majority of light bulb sockets in homes and offices throughout the United States.

Figure 1:
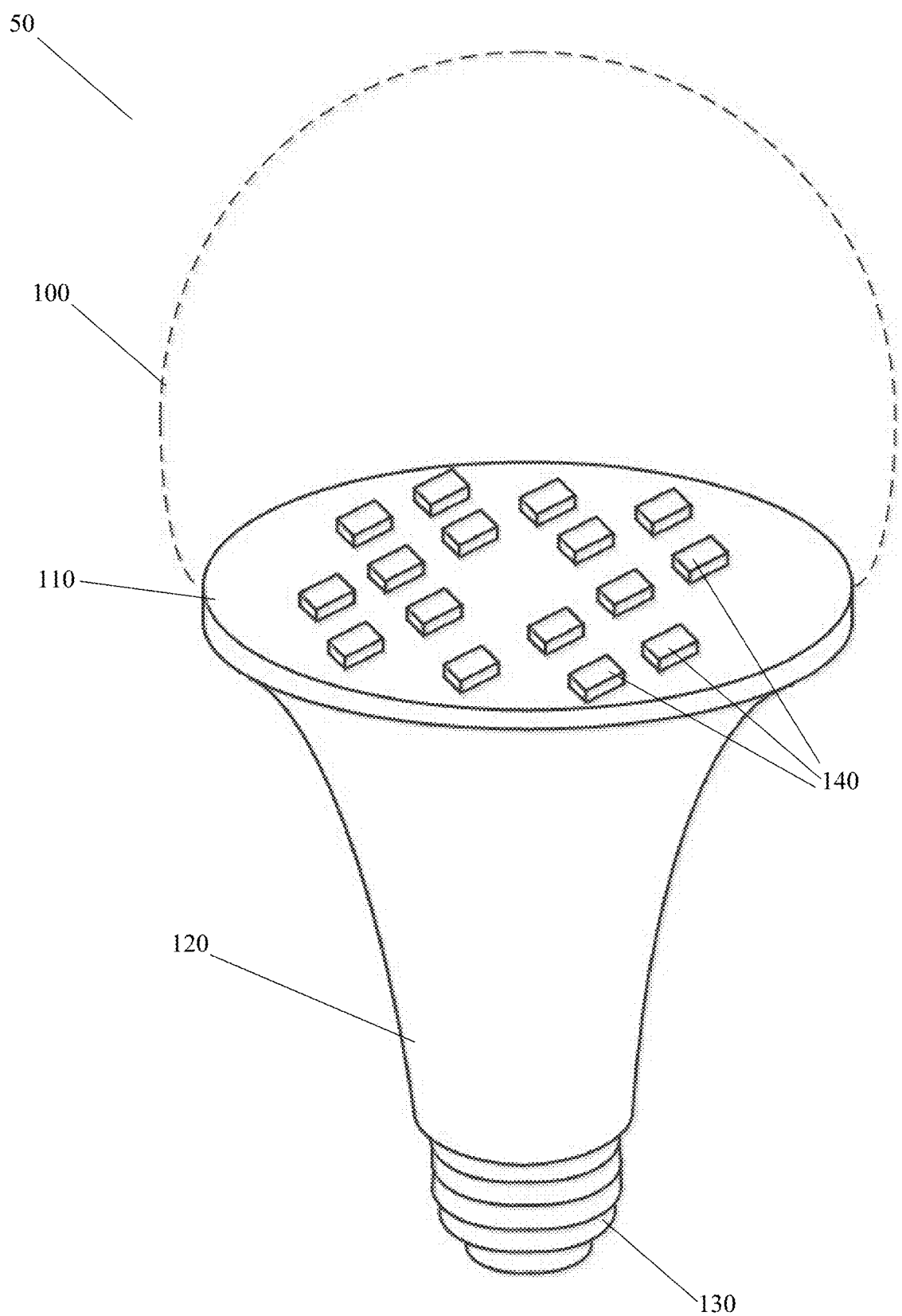
FIG. 1 is a schematic drawing showing a cross-section of an example embodiment as a light bulb.
Figure 3:
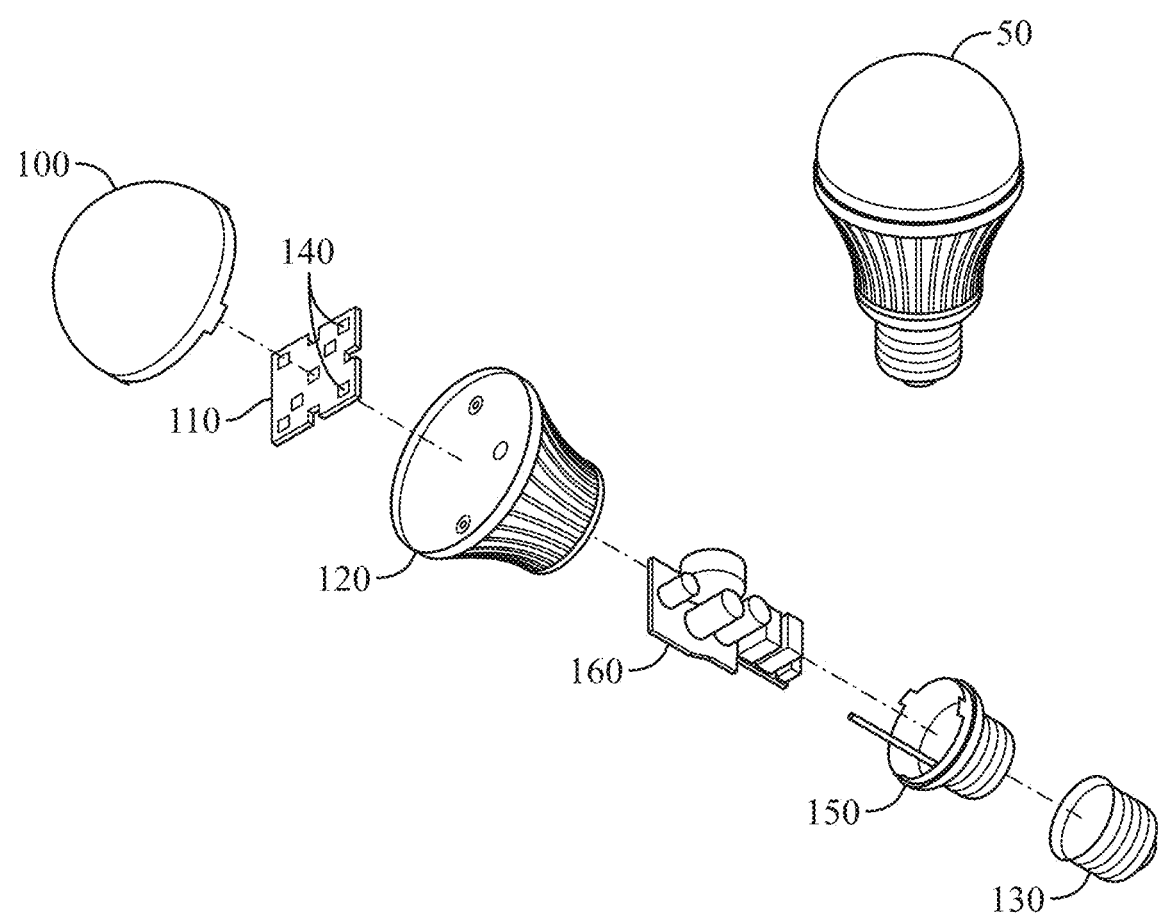
FIG. 3 is an exploded view illustrating the common components of an example embodiment as a light bulb.

FIG. 1 is a schematic diagram showing the structure of a typical light-emitting diode (LED) bulb constructed with an E26 base. As shown in FIG. 1, a typical LED bulb 50 is composed of a variable number of LED's 140 contained on an LED panel 110, a transparent or semitransparent glass or plastic globe 100, a heatsink 120, and a base 130. The LED's 140 in this example embodiment are a combination of NIR and non-NIR LED's. It is also feasible for an embodiment to utilize a single LED that emits both visible spectrum light and NIR light. FIG. 3 shows additional internal components, a driver 160 and an electrical connector 150. The components shown in FIGS. 1 and 3 are typical light bulb components that are well-known in the art and are not discussed further here.

Figure 2:
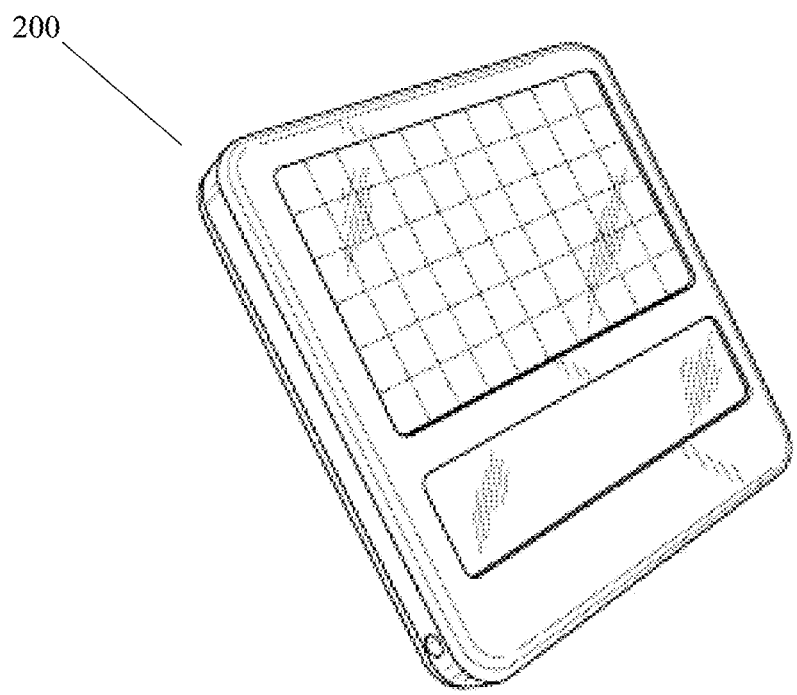
FIG. 2 is an illustration of an alternate form factor for an example embodiment as a light therapy device.

FIG. 2 is an illustration of another possible embodiment, in this case as a light therapy device 200. The embodiment shown in FIG. 2 has an approximately rectangular shape similar to a tablet computer. The front face of the device contains LED's behind a diffuser, either NIR LED's or a combination of NIR and non-NIR LED's. The device is constructed such that the LED's emit light primarily in a single direction. The device can be positioned and directed to provide light therapy to a specific location, such as a patient's eyes. FIG. 2 is one example of a light therapy device, in particular a small, portable device. Many other sizes and shapes of light therapy devices exist and are possible, such as full size lamps which include floor, table, wall, and ceiling-mounted units, and all such devices are contemplated and compatible with this invention.

The LED's within a typical LED bulb produce most of their light in the visible spectrum. The most common configurations attempt to reproduce a white light that is similar to previous generations of lighting solutions.

In one embodiment of the present invention, one or more of the LED's contained within an LED bulb emit light primarily in the near-infrared (NIR) spectrum, as defined as light wavelengths between 700-1,400 nanometers.

According to one aspect of the invention, the radiant output of the NIR LED elements is approximately 10-50% of the total radiant output, or between a ratio of 1 to 9 up to 1 to 1 of NIR LED's to non-NIR LED's. It is also feasible and contemplated within this invention for a single LED to emit useful amounts of both visible spectrum light and NIR light.

According to another aspect of the invention, one or more of the LED's contained within an LED bulb or light therapy device are sized differently than other LED's. Such LED's that are sized differently also emit light that is primarily of a different wavelength than other LED's. Such LED's that are sized differently may also have different power requirements and require a separate driver than other LED's.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein and illustrated in the figures, can be arranged, substituted, combined, separated, and designed in a wide variety of different configurations, all of which are contemplated herein.

What is claimed is:

1. A light source shaped like a light bulb having a standard E26 base, the light source comprising:

a plurality of LEDs, some of the LEDs providing visible light;

at least one LED configured to provide only near infrared (NIR) electromagnetic radiation of wavelengths peaked at 850 nanometers;

a panel configured to support the plurality of LEDs; and a standard E26 base electrically cooperative with the panel.

2. The light source of claim 1, wherein the panel is round.

3. The light source of claim 1, further comprising:

at least one LED configured to provide only NIR electromagnetic radiation of wavelengths peaked at 780 nanometers.

4. The light source of claim 1, further comprising:

at least one LED configured to provide only red light of wavelengths peaked at 670 nanometers.

5. The light source of claim 1, wherein the visible light is substantially white light.

6. The light source of claim 1, wherein the ratio of LEDs emitting NIR electromagnetic radiation to LEDs providing visible light is between 1 to 9 and 1 to 1.

* * * * *